(12) United States Patent
Kraus et al.

(10) Patent No.: US 8,600,008 B2
(45) Date of Patent: Dec. 3, 2013

(54) SYSTEM AND METHOD OF PROVIDING AN EMERGENCY CONTACT PARTY LINE

(76) Inventors: Mark Kraus, Bloomfield Hills, MI (US); Paul Toenjes, Grosse Pte. Farms, MI (US)

( * ) Notice: Subject to any disclaimer, the term of this patent is extended or adjusted under 35 U.S.C. 154(b) by 19 days.

(21) Appl. No.: 13/172,997

(22) Filed: Jun. 30, 2011

(65) Prior Publication Data
US 2012/0002791 A1    Jan. 5, 2012

Related U.S. Application Data

(60) Provisional application No. 61/359,959, filed on Jun. 30, 2010.

(51) Int. Cl.
*H04M 11/04* (2006.01)

(52) U.S. Cl.
USPC .............................................. 379/37; 379/40

(58) Field of Classification Search
USPC ................. 379/37–40, 42; 340/500, 502, 506
See application file for complete search history.

(56) References Cited

U.S. PATENT DOCUMENTS

| | | | |
|---|---|---|---|
| 5,166,972 A | 11/1992 | Smith | |
| 6,366,646 B1 | 4/2002 | Miller | |
| 6,650,746 B1 | 11/2003 | Groen et al. | |
| 6,658,104 B1 | 12/2003 | Carrion et al. | |
| 6,703,930 B2 * | 3/2004 | Skinner | 340/539.11 |
| 6,735,285 B2 | 5/2004 | Orwick et al. | |
| 6,807,564 B1 | 10/2004 | Zellner et al. | |
| 6,965,868 B1 | 11/2005 | Bednarek | |
| 7,126,472 B2 | 10/2006 | Kraus et al. | |
| 7,477,142 B2 | 1/2009 | Albert et al. | |
| 2002/0130002 A1 | 9/2002 | Hopkins et al. | |
| 2004/0145481 A1 * | 7/2004 | Dilbeck et al. | 340/573.1 |
| 2005/0136885 A1 | 6/2005 | Kaltsukis | |
| 2007/0083918 A1 | 4/2007 | Pearce et al. | |
| 2007/0171898 A1 | 7/2007 | Salva | |
| 2007/0290830 A1 | 12/2007 | Gurley | |
| 2008/0063152 A1 * | 3/2008 | Kraus et al. | 379/39 |
| 2009/0070682 A1 | 3/2009 | Dawes et al. | |
| 2009/0086943 A1 | 4/2009 | Jain et al. | |
| 2010/0285771 A1 * | 11/2010 | Peabody | 455/404.2 |

* cited by examiner

*Primary Examiner* — Quoc D Tran
(74) *Attorney, Agent, or Firm* — Dickinson Wright PLLC

(57) ABSTRACT

A system and method for providing an emergency contact party telephone line in response to an emergency. The system includes a user device (21) and a monitoring database (22), which communicate with one another over the Internet (23). A plurality of contacts and contact methods are stored on the monitoring database (22). The contact methods for each contact are arranged in a hierarchy according to priority. When the user device (21) establishes an emergency condition, it communicates the emergency condition to the monitoring database (22). The monitoring database (22) then establishes a support line, similar to a conference call line. Once the support line is set up, the monitoring database (22) sends a notification message of the emergency to the contacts through a first contact method. The monitoring database (22) then sends another notification message through a second contact method different to the first contact method to each of the contacts who did not respond to the first notification message.

11 Claims, 7 Drawing Sheets

SYSTEM AND METHOD OF PROVIDING AN EMERGENCY CONTACT PARTY LINE

CROSS REFERENCE TO RELATED APPLICATION

This application claims the benefit of U.S. provisional application Ser. No. 61/359,959 filed Jun. 30, 2010.

BACKGROUND OF THE INVENTION

1. Field of the Invention

A method of providing an emergency contact party telephone line in response to an emergency.

2. Description of the Prior Art

Various methods and devices are available for providing emergency response to a user. One such method is shown in U.S. Pat. No. 5,166,972, issued to Dawn Smith on Nov. 24, 1992 (hereinafter referred to as "Smith '972"). The Smith '972 method starts with the steps of providing a user device and providing a monitoring database including a plurality of contacts and including a first contact method for contacting each contact. The method continues with the step of establishing communication between the user device and the monitoring database. The method then proceeds with the step of establishing an emergency condition with the user device. Upon the emergency condition being established, the method continues with the step of sending an emergency notification from the user device to the monitoring database. Once the monitoring database receives the emergency notification, the method continues with the step of automatically establishing a support line with the monitoring database. Finally, the method ends with the steps of automatically sending a notification message to each of the contacts with the first contact method and automatically providing each of the contacts that accepted the notification message through the first contact method with a route to connect to the support line.

While the Smith '972 method sets up a support line in response to an emergency, it is unable to reach out to contacts who do not accept the notification message through the first contact method. There is a continuing need for an improved method for providing an emergency response to a user.

SUMMARY OF THE INVENTION

The subject invention is for such a method and further including the step of automatically sending a notification message through the second contact method different than the first contact method to each of the contacts that failed to respond to the notification message sent through the first contact method.

ADVANTAGES OF THE INVENTION

The subject invention is advantageous because it is able to establish communication with the contacts who did not respond, or answer, the notification message sent through the first contact method. For example, the first contact method could be a home phone number for calling the contact and the second contact method could be a cellular phone number for calling the contact. When the user device sends a notification message to the monitoring database, the monitoring database will first send the notification message to the contact through the first contact method. If the first contact does not respond to the notification message, then the monitoring database will send the notification message to the contact through the second contact method. This increases the opportunities for each of the contacts to be connected to the support line.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE ENABLING EMBODIMENTS

Figure 1:
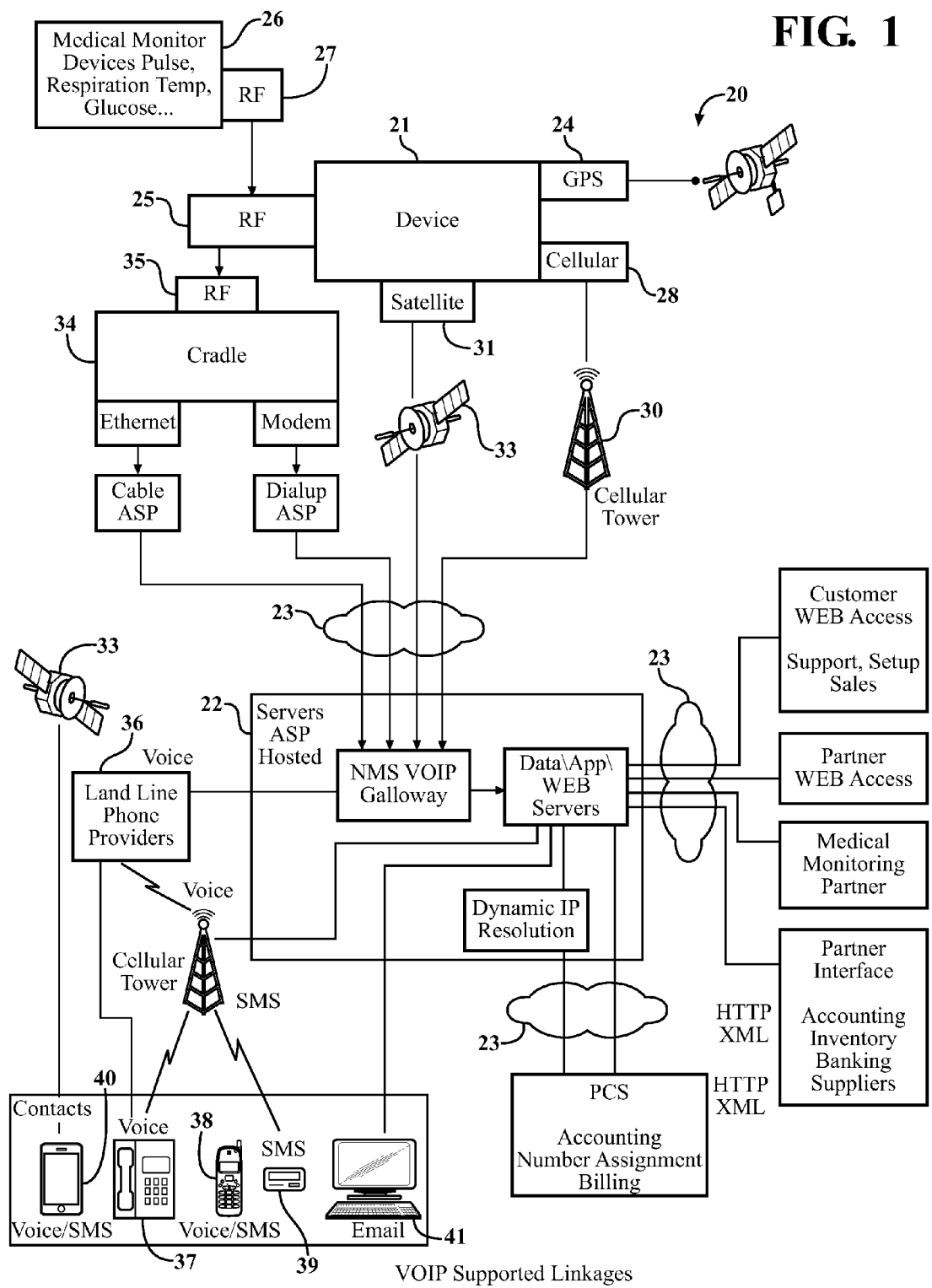
FIG. 1 is a graphical representation of an emergency alert system having a user device and a monitoring database communicating via the Internet.

Referring to the Figures, wherein like numerals indicate corresponding parts throughout the several views, an emergency alert system 20 for establishing an emergency contact party telephone line is generally shown in FIG. 1. The emergency alert system 20 includes a user device 21 carried by a user (not shown) and a monitoring database 22. As will be discussed in greater detail below, the user device 21 and monitoring database 22 communicate with each other via Internet Protocols (IP) over the Internet 23. It is to be appreciated that IP includes transmission control protocols (TCP) and any other connectionless, packet switching protocol that may be employed to communicate across the Internet 23. The preferred Internet Protocol is TCP/IP, but the subject invention contemplates use with other Internet Protocols, such as fibre channel protocol (FCP) or file transfer protocol (FTP). The Internet 23 refers to a system of interconnected networks that connects computers around the world, as understood by those skilled in the art. The Internet 23 is illustrated in FIG. 1 as being cloud-shaped and interconnecting various components, each of which will be discussed in further detail below.

Referring to FIG. 1, the emergency alert system 20 is schematically illustrated with the user device 21 and the monitoring database 22 being connected to one another via the Internet 23. The user device 21 includes a GPS receiver 24, or a global positioning system receiver, for obtaining the coordinates of the user device 21 and a user RF module 25. The emergency alert system 20 also includes biometric equipment 26 for monitoring the user. The biometric equipment 26 includes a biometric RF module 27 that establishes communication with the user RF module 25 via radio-frequency (RF) signals.

The user device 21 of the exemplary embodiment has an IP address and can connect to the Internet 23 in three different ways: a cellular connection, a satellite connection and a cradle connection. To facilitate the cellular connection, the user device 21 includes a cellular modem 28 and a cellular antenna 29 for connecting to a cellular network through a cellular tower 30. To facilitate the satellite connection, the user device 21 includes a satellite modem 31 and a satellite antenna 32 for connecting to a satellite network through a satellite 33. To facilitate the cradle connection, the emergency alert system 20 includes a cradle 34 that is connected to the Internet 23. The cradle 34 includes a cradle RF module 35 for communicating with the user device 21 via RF signals. Preferably, the user device 21 only communicates with one of the cellular network, satellite network or the cradle 34 at any given instant. However, there may be times when communicating over all three is desirable. The cellular modem 28, satellite modem 31 and cradle 34 are all capable of transmitting signals based on IP and support Voice-Over Internet Protocol (VoIP), which will be described in more detail below. The VoIP connections are shown as thicker linkages in FIG. 1. It should be appreciated that the user device 21 could alternatively be connected to the Internet 23 in a number of different ways other than those listed above, including but not limited to through a wireless local area network (WLAN).

The monitoring database 22 has an IP address for communicating with the user device 21 over the Internet 23. The monitoring database 22 also includes a gateway that is connected to a public switched telephone network (PSTN 36) for transmitting voice messages and is preferably connected to voice/data servers for transmitting voice and data messages over the Internet 23. The monitoring database 22 is preferably a server.

Identifications for a plurality of user devices 21 and user information associated with each of the user devices 21 are stored on the monitoring database 22. The user information includes a list of contacts to be contacted in an emergency. The list of contacts may be modified by the user at any time through any web-based application. Additionally, selected contacts may have administrator level access to update and modify the list of contacts on behalf of the user. The monitoring database 22 also includes at least one contact method for contacting each of the contacts. The contact methods may include telephone phone numbers for calling the contact, telephone numbers for sending short messaging service (SMS) messages to the contact, pager numbers for sending pager messages to the contact or email addresses for sending emails to the contact. When there is more than one contact method for a single contact, the contact methods are arranged in a hierarchy, or a priority order, according to priority with a first contact method being at the top of the hierarchy. Additionally, the monitoring database 22 may arrange the hierarchy according to the time of day or the day of the week. For example, a home telephone number for calling the contact could be at the top of the hierarchy during weekends, holidays or evenings, and a work telephone number could be at the top of the hierarchy during work days. The user may access and modify the hierarchy of contact methods for each contact through any web-based application. As will be discussed in further detail below, the monitoring database 22 will send a notification message to the contacts through the various contact methods according to their order of priority.

One advantage of the system is the variety of contact methods that may be used to communicate with the contacts. In FIG. 1, the monitoring database 22 is illustrated communicating to the PSTN 36 for communicating with a landline telephone 37; to a cellular network for communicating with a cellular phone 38 or a pager 39; to a satellite 33 for communicating with a satellite phone 40; and to the Internet 23 for transmitting email messages or other web based information to any internet-connected device 41.

Additional information about the user may also be stored on the monitoring database 22. A geofence, or a predetermined range of longitudinal and latitudinal coordinates that the user must remain within can be stored on the monitoring database 22. The geofence can be set up or modified by the user or any contact with administrator status. The GPS receiver 24 in the user device 21 continuously monitors the longitudinal and latitudinal coordinates of the user device 21 and compares those coordinates to the geofence.

The user device 21 also includes a memory source 42 for storing the IP address of the user device 21 and the IP address of the monitoring database 22. The memory source 42 may include read-only memory (ROM), electrically erasable programmable ROM (EE-PROM), random access memory (RAM), flash, or any other type of memory capable of storing information. Those skilled in the art recognize that the IP addresses are assigned in blocks to service providers. The block of IP addresses are then divided again and assigned by the service providers to their customers, including the user device 21.

As explained above, the user RF module 25 of the user device 21 communicates with the biometric RF module 27 of the biometric equipment 26 and the cradle RF module 35 of the cradle 34. Preferably, the RF modules 43 communicate with each other using Bluetooth® protocols. However, any other RF signals may alternatively be used. Those skilled in the art of radio frequency transmission recognize that Bluetooth® is a standard for transmitting radio frequency signals using a frequency hopping spread spectrum such that wires are not necessary. The biometric equipment 26 transmits biometric data about the user to the user device 21 through the biometric and user RF modules 25, 27, and the user device 21 may then store the biometric data on the memory source 42. Alternatively, the user device 21 may transmit the biometric data to the monitoring database 22, which stores the data. If the user encounters a medical emergency, the biometric data on either the user device 21 or the monitoring database 22 will assist in the assessment of the medical emergency.

Figure 2:
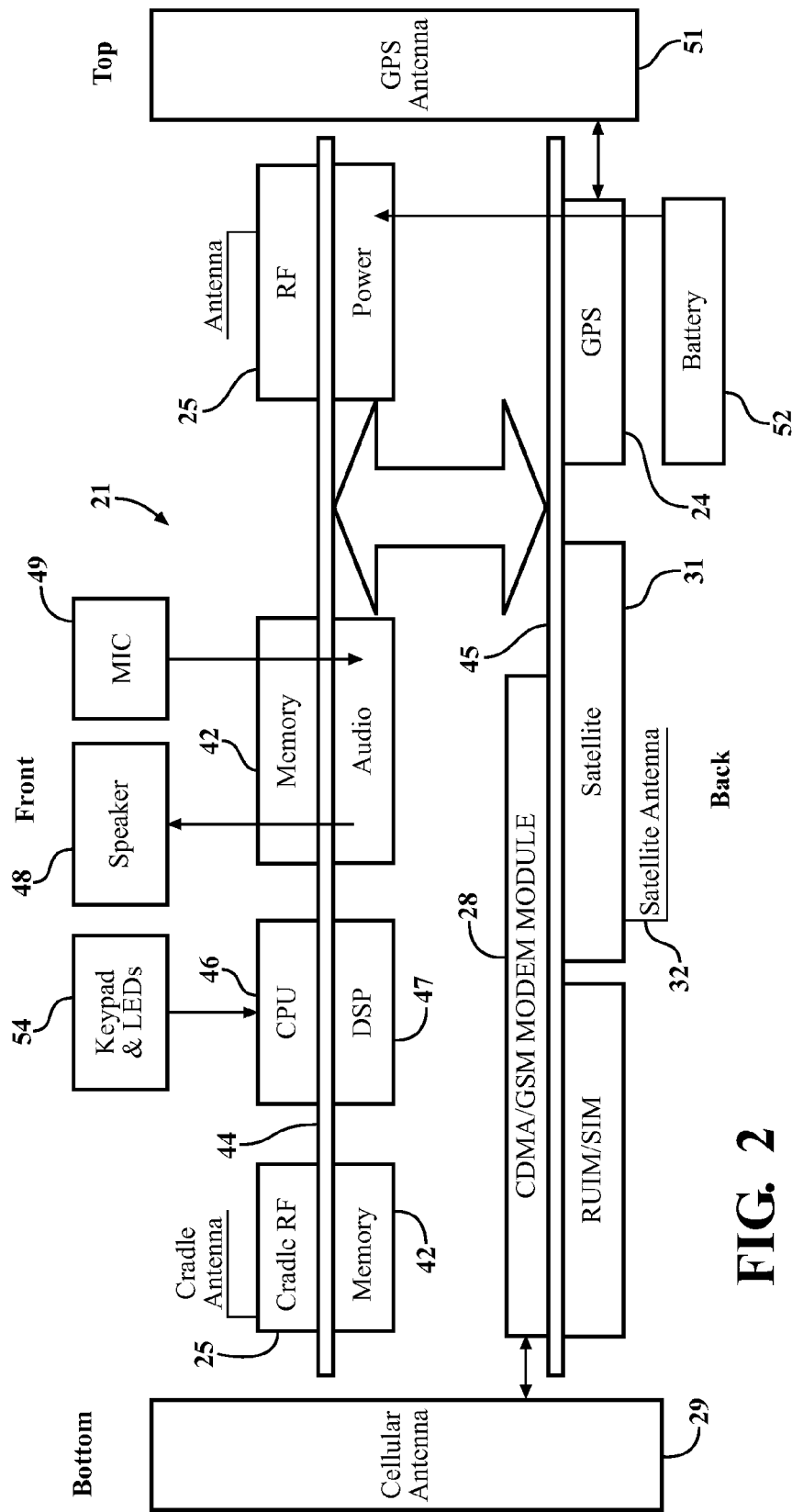
FIG. 2 is a schematic view of the user device.
Figure 3:
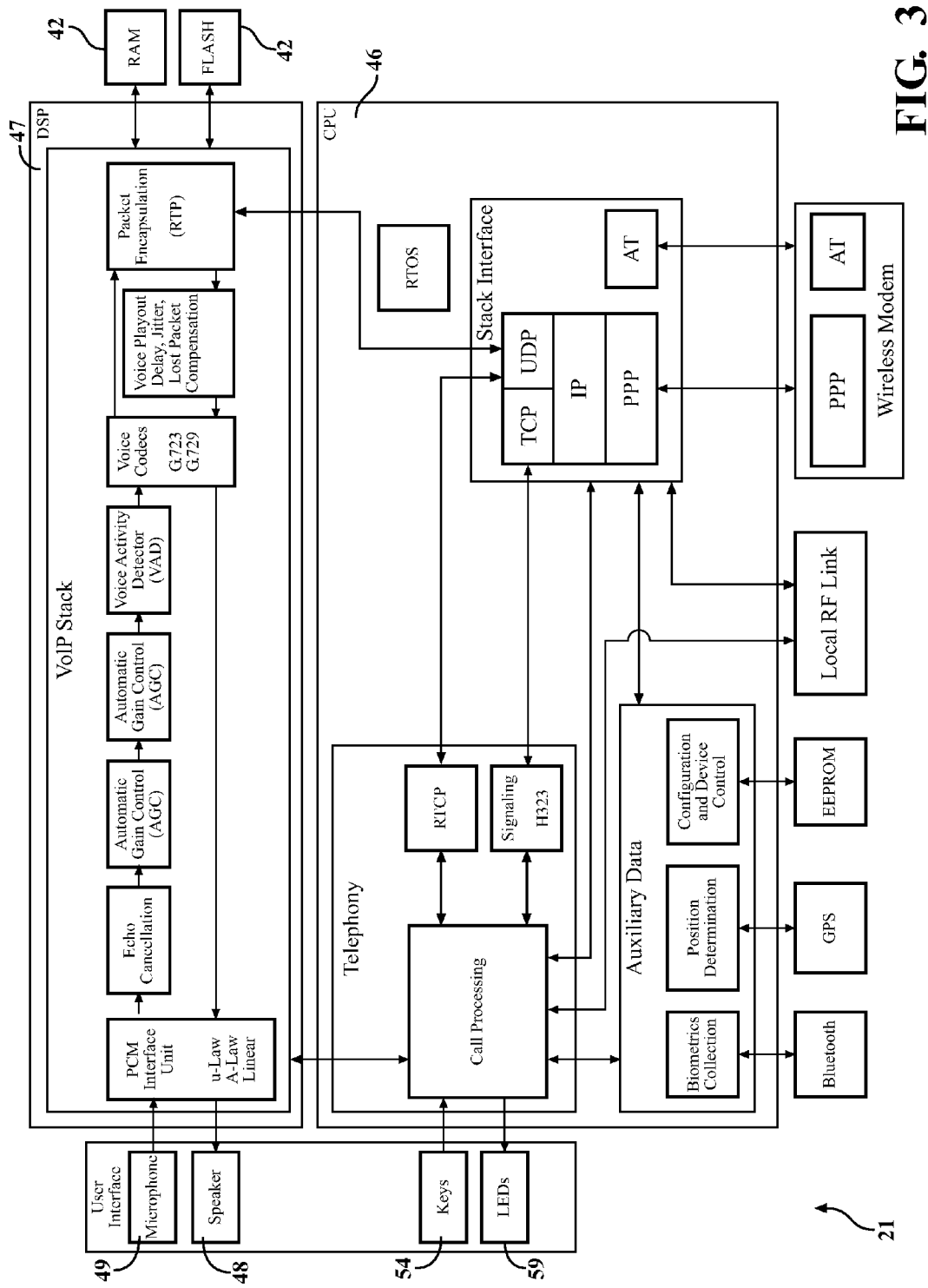
FIG. 3 is another schematic view of the user device.

The exemplary embodiment of the user device 21 is schematically illustrated in FIGS. 2 and 3. The exemplary embodiment includes a pair of printed circuit boards—a main board 44 and a secondary board 45—for carrying the internal components of the user device 21. The main board 44 includes a central processing unit (CPU 46) for controlling the user device 21 and the memory source 42. The main board 44 may also include a digital signal processor (DSP 47) for generating or receiving digital signals transmitted from or to the user device 21. The user RF module 25 for communicating with the cradle 34 and biometric equipment 26 may also be disposed on the main board 44. The user device 21 may include a single user RF module 25 or multiple user RF modules 25 as is necessary. An RF antenna is connected to each user RF module 25 for transmitting or receiving the RF signals. A user speaker 48 and a user microphone 49 may also be connected to the main board 44 for transmitting sounds and audio communications to and from the user device 21.

The cellular modem 28, the cellular antenna 29, the satellite modem 31, the satellite antenna 32, the GPS receiver 24 and a GPS antenna 50 are all mounted on the secondary board 45. Both the cellular modem 28 and the satellite modem 31 are in electrical communication with the CPU 46 for transmitting signals through the cellular and satellite connections respectively. The GPS receiver 24 is also in electrical communication with the CPU 46 and the memory source 42 for storing the longitudinal and latitudinal coordinates of the user device 21. The GPS antenna 50 receives signals from a plurality of navigation satellites 51 to determine the longitudinal and latitudinal coordinates of the user device 21.

The user device 21 further includes a power supply 52 for providing power to the CPU 46, the memory source 42, and the other components of the user device 21. The power supply 52 is preferably a battery, but alternatively could be a fuel cell or any other source of electricity.

The user device 21 is preferably worn by the user, but could be placed in the pocket of the user or somewhere in the user's house. The user device 21 includes a housing 53 surrounding the main and secondary boards 44, 45. The housing 53 is preferably formed of plastic, but may be formed of any other durable, lightweight material to be carried by the user. Preferably, the GPS receiver 24, the user RF module 25, the cellular modem 28, the cellular antenna 29, the satellite modem 31, the satellite antenna 32, the microphone, the speaker and the power supply 52 are all also disposed within the housing 53. The housing 53 is preferably watertight to prevent water from entering the user device 21 and damaging the components therein.

The user device 21 also includes a user input 54 for allowing a person to signal an emergency condition. The user input 54 could be buttons 54, a keypad, a switch, a touch-screen display 55, or any other input device. As will be discussed in further detail below, the user input 54 could be used to send an emergency signal to the monitoring database 22, to cancel an emergency or to facilitate any other communication between the user and the monitoring database 22.

Figure 4:
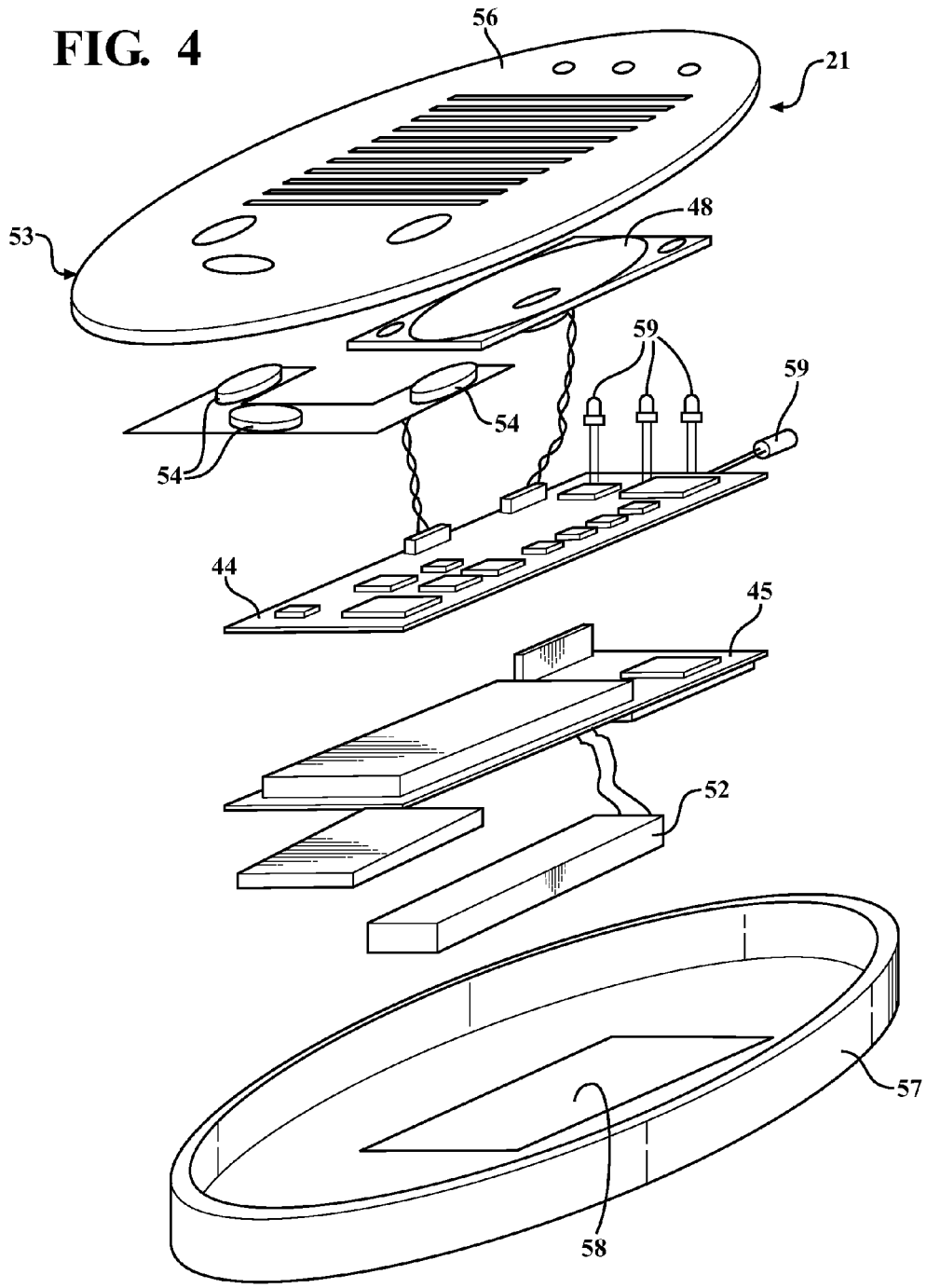
FIG. 4 is an exploded view of a first embodiment of the user device.

A first exemplary embodiment of the user device 21 is generally shown in FIG. 4. The housing 53 of the first exemplary embodiment is elliptically shaped and includes a top shell 56 and a bottom shell 57. The bottom shell 57 has an access door 58 for accessing the power supply 52. In the first exemplary embodiment, the user input 54 includes three push buttons 54. The first exemplary embodiment further includes three light emitting diodes (LEDs 59). The LEDs 59 could alert the user that the power supply 52 is running low on electricity, that the user device 21 has sent out an emergency signal to the monitoring database 22 or that the user device 21 is currently communicating with the monitoring database 22.

Figure 5:
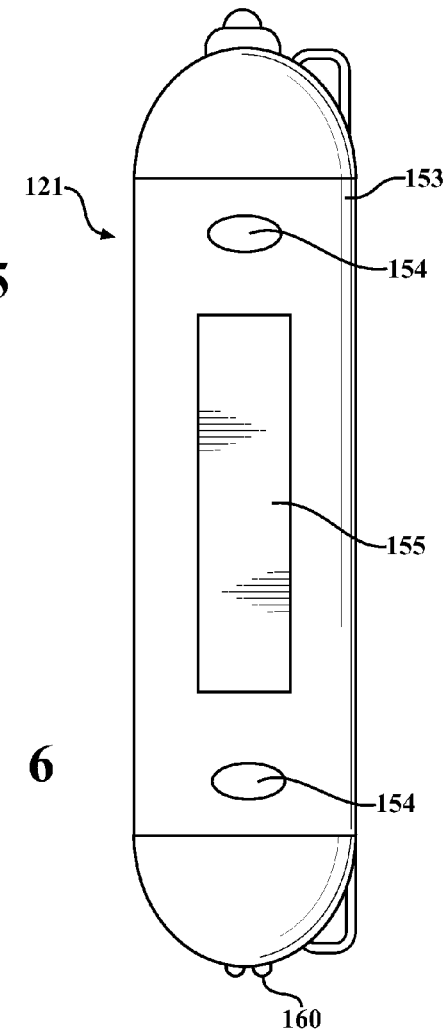
FIG. 5 is a front view of a second embodiment of the user device.

A second exemplary embodiment of the user device 121 is generally shown in FIG. 5. The housing 153 of the second exemplary embodiment is generally cylindrically shaped and includes a display 155 that replaces the LEDs 59 of the first exemplary embodiment. The display 155 could be a liquid crystal display (LCD), an LED monitor, or any other display. The user input 154 of the second exemplary embodiment is two push buttons 154 that are used to both activate and cancel emergency notifications. An ear bud plug 160 is included for connecting an ear bud or any other speaker to the user device 121.

Figure 6:
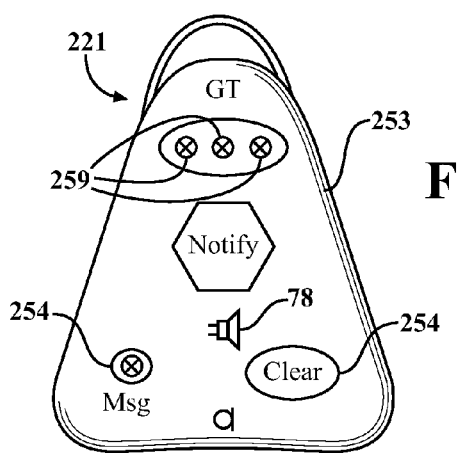
FIG. 6 is a front view of a third embodiment of the user device.

A third exemplary embodiment of the user device 221 is generally shown in FIG. 6. The housing 253 of the third exemplary embodiment is triangularly shaped, and the user input 254 includes three push buttons 254. One of the push buttons 254 establishes an emergency condition and the other cancels the emergency condition and one sends a non-emergency message to the monitoring database 22. A plurality of LEDs 259 for alerting the user of messages on the user device 221 are also included on the housing 253 of the third exemplary embodiment.

Figure 7:
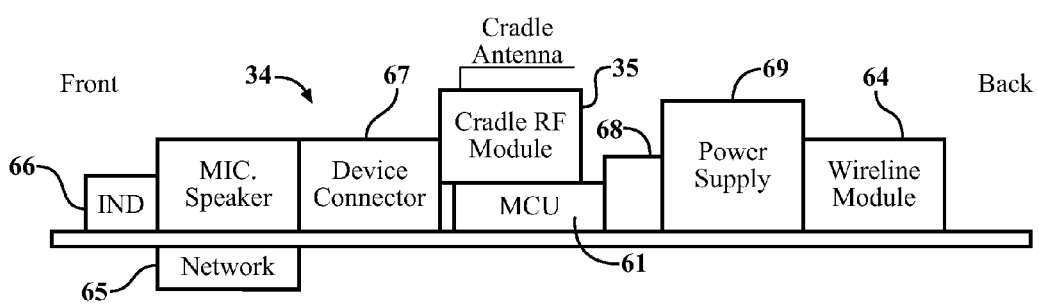
FIG. 7 is a side view of cradle.

FIG. 7 shows a schematic views of the exemplary embodiment of the cradle 34. The cradle 34 includes a main control unit (MCU 61) communicating with a cradle microphone 62, a cradle speaker 63 and the cradle RF module 35. In the exemplary embodiment, the cradle 34 includes both a cradle modem 64 for connecting to the Internet 23 through the PSTN 36 and a network card 65 for connecting to the Internet 23 through an Ethernet connection. When the cradle modem 64 is used, the cradle 34 uses the PSTN 36 to access the Internet 23 through a service provider, whereas, when the network card 65 is used, the cradle 34 is directly connected to the Internet 23 through a cable connection, a digital subscriber lines (DSL) connection or any other type of Ethernet connection to the Internet 23.

The cradle 34 further includes an indicator 66 to alert the user of the status of the cradle 34 and/or the user device 21 and a device connector 67. The user device 21 may be inserted into a device connector 67 for connecting to the cradle 34. When the cradle 34 and user device 21 are connected, the cradle 34 charges the power supply 52 of the user device 21, and the user can communicate with the monitoring database 22 directly through the cradle 34. Optionally, the cradle 34 could include a secondary connector 68 for receiving and charging additional power supplies 52. This ensures that the user will always have a charged power supply 52 available when the user device 21 is not charging in the cradle 34. The device connector 67 may be connected to a module or a base for receiving the user device 21. The cradle 34 further includes a cradle power supply 69 that is preferably electrically connected to an AC adapter for powering the cradle 34 and for charging the user device 21.

In the exemplary embodiments, three different events can trigger the user device 21 to send an emergency notification to the monitoring database 22. The first event is the user signaling an emergency condition with the user input 54 of the user device 21. The second event is the biometric equipment 26 sensing an emergency condition. The third event is the user device 21 leaving the predetermined geofence area.

The biometric equipment 26 includes at least one sensor for sensing an emergency in the user. The biometric equipment 26 could include a heart rate sensor for monitoring the user's pulse, a resperation sensor for monitoring the user's breathing, a thermometer for measuring the user's temperature, a glucose monitor for measuring the user's blood glucose levels or any other biometric measuring device. If the biometric senses an emergency condition, it communicates the emergency condition to the user device 21 through the RF signals. The user device 21 then sends an emergency notification to the monitoring database 22 through the Internet 23.

Figure 8A:
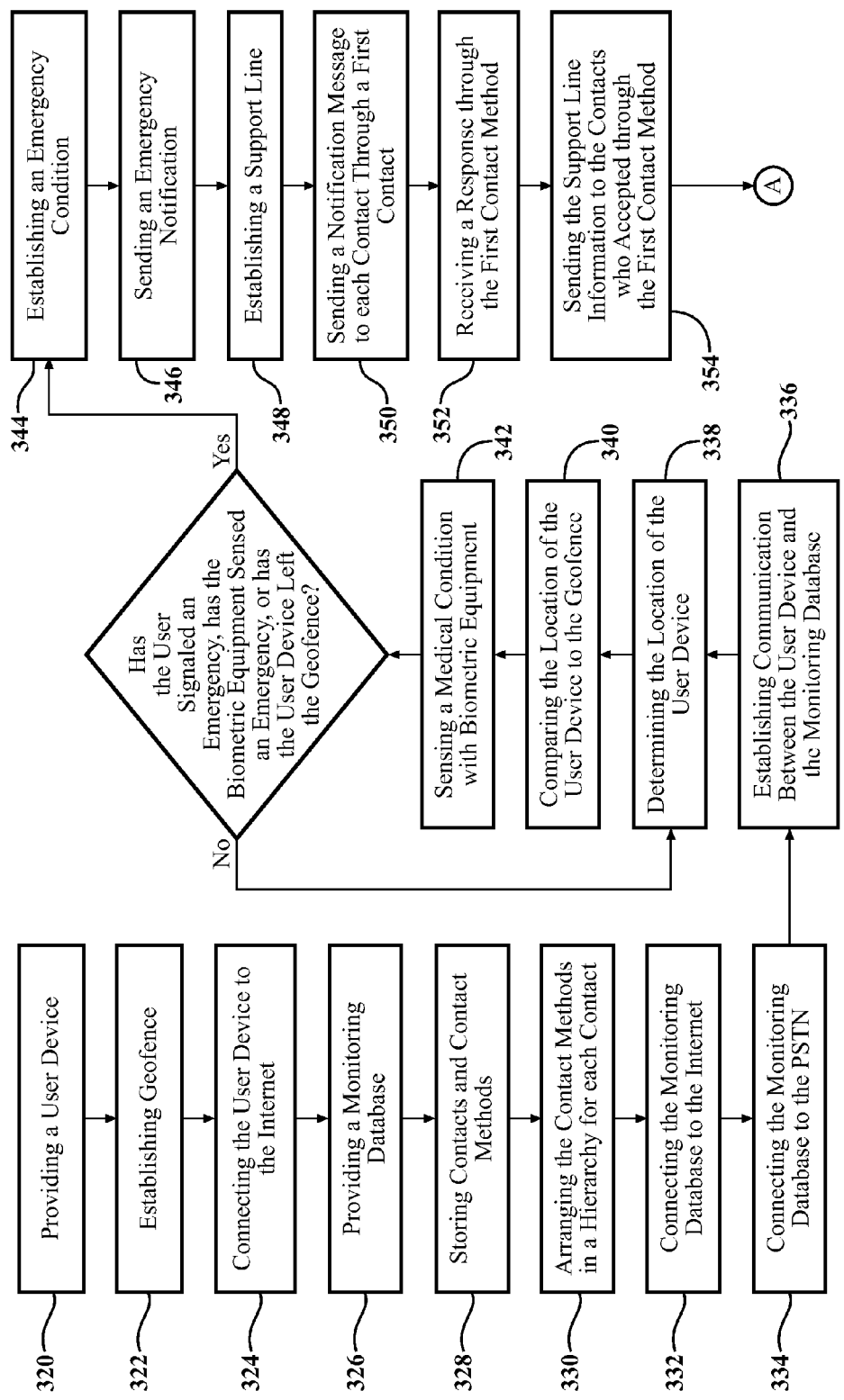
FIG. 8 is a flowchart illustrating a method of establishing an emergency contact party line.
Figure 8B:
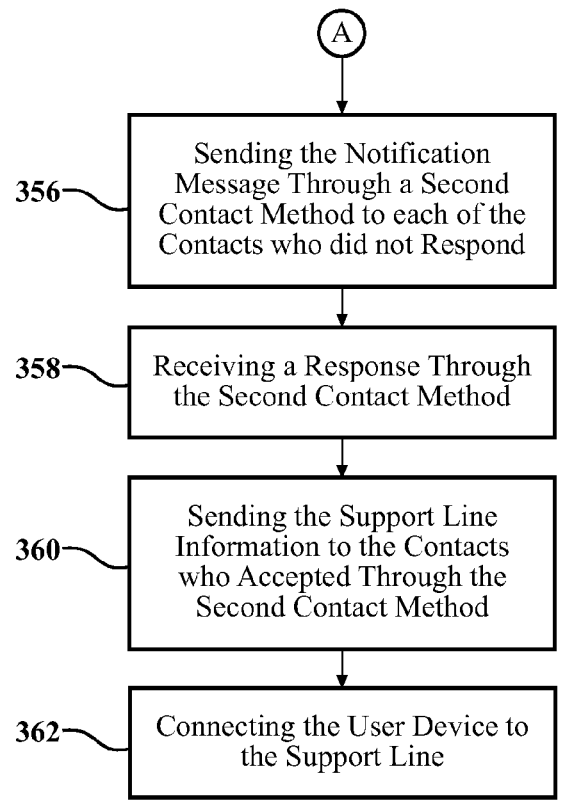

The subject invention also affords a method of providing an emergency contact party telephone line in response to an emergency. The method is illustrated in a flow chart shown in FIG. 8.

The method begins with the step 320 of providing a user device 21 including a power supply 52, a user input 54, biometric equipment 26, a user microphone 49 and a user speaker 48. The method continues with the step 322 of establishing a geofence of longitudinal and latitudinal coordinates for containing the user device 21. Next, the method proceeds with the step 324 of establishing an Internet 23 Protocol (IP) address for the user device 21 through a cellular network connection, a satellite connection or a cradle connection to connect the user device 21 to the Internet 23.

The method proceeds with the step 326 of providing a monitoring database 22. The method then continues with the step 328 of storing a plurality of contacts to be contacted and a plurality of contact methods for contacting each contact. The contact methods could be a phone number for calling the contact, a phone number for sending an SMS message to the contact, a pager 39 number for sending a pager 39 message to the contact or an email address for sending an email address to the contact. The method proceeds with the step 330 of arranging the contact methods a hierarchy, or a priority order, and including a first contact method and a second contact method. Once the hierarchy of contact methods is established for each contact, the method continues with the step 332 of establishing an Internet Protocol (IP) address for the monitoring database 22 to connect the monitoring database 22 to the Internet 23. It should be appreciated that the monitoring database 22 can be connected to the Internet 23 through any desired method. The method then proceeds with the step 334 of connecting the monitoring database 22 to the PSTN 36.

Once both the user device 21 and the monitoring database 22 are connected to the Internet 23, the method continues with the step 336 of establishing communication over the Internet 23 between the monitoring database 22 and the user device 21. Next, the method continues with the step 338 of determining the longitudinal and latitudinal coordinates of the user device 21 with the GPS receiver 24. The method then continues with the step 340 of comparing the longitudinal and latitudinal coordinates of the user device 21 to the geofence. Either the user device 21 or the monitoring database 22 could do the comparing of the longitudinal and latitudinal coordinates of the user device 21 to the geofence. Further, the method includes the step 342 of sensing a medical condition with the biometric equipment 26.

As explained above, an emergency condition can be established through the user input 54, the biometric equipment 26 or the geofence. Therefore, the method continues with the step 344 of establishing an emergency condition with the user device 21 in response to the user of the user device 21 signaling an emergency with the user input 54, the biometric equipment 26 sensing an emergency or the user device 21 leaving the predetermined geofence. Once an emergency condition has been established by the user device 21, the method continues with the step 346 of automatically sending an emergency notification through the Internet 23 from the user device 21 to the monitoring database 22.

Once the monitoring database 22 receives the emergency notification from the user device 21, the method continues with the step 348 of automatically establishing a support line, or a conference bridge, with the monitoring database 22. The monitoring database 22 can either be the host of the support line, or it can work with a third party provider to establish the support line. In one embodiment, the monitoring database 22 or the third party provider determines a call-in number and a password to gain access to the support line.

Once the support line has been established, the method continues with the step 350 of automatically sending a notification message with the monitoring database 22 to each of the contacts through the first contact method. As explained above, the first contact method is the contact method at the top of the hierarchy of the associated contact in the monitoring database 22 at the time of the emergency notification.

After the notification message has been sent out to the contacts, the monitoring database 22 waits a predetermined amount of time for the contacts to respond. During the predetermined amount of time, the method continues with the step 352 of receiving with the monitoring database 22 an accepted response or a rejected response from the contacts. The method then continues with the step 354 of automatically sending the call-in number and the password of the support line through the first contact method to each of the contacts that accepted the notification message. Alternatively, the monitoring database 22 can then directly connect each of the contacts who accept the notification message to the support line.

After the predetermined amount of time has elapsed, the monitoring database 22 could re-try sending the notification message through the first contact method to the contacts who failed to respond. After the monitoring database 22 is through attempting to establish communication with those unresponsive contacts through the first contact method, the method continues with the step 356 of automatically sending the notification message with the monitoring database 22 through a second contact method different from the first contact method to each of the contacts who failed to respond to the notification message from the first contact method. Again, the monitoring database 22 waits for a predetermined amount of time for the contacts to respond. During that predetermined amount of time, the method proceeds with the step 358 of receiving with the monitoring database 22 one of an accepted response and a rejected response from the contacts. The method then continues with the step 360 of automatically sending the call-in number and the password of the support line with the second contact method to each of the contacts that accepted the notification message through the second contact method. Alternatively, the monitoring database 22 can then directly connect each of the contacts who accept the notification message to the support line.

The monitoring database 22 continues to try to establish communication with each of the contacts through the different contact methods until all of the contact methods for a contact are exhausted. The method is complete with the step 362 of connecting the user device to the support line. Once connected to one another on the support line, the contacts and the user can discuss the best way to respond to the emergency condition.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

ELEMENT LIST

| Element Symbol | Element Name |
| --- | --- |
| 20 | emergency alert system |
| 21 | user device |
| 22 | monitoring database |
| 23 | Internet |
| 24 | GPS receiver |
| 25 | user RF module |
| 26 | biometric equipment |
| 27 | biometric RF module |
| 28 | cellular modem |
| 29 | cellular antenna |
| 30 | cellular tower |
| 31 | satellite modem |
| 32 | satellite antenna |
| 33 | satellite |
| 34 | cradle |
| 35 | cradle RF module |
| 36 | PSTN |
| 37 | landline telephone |
| 38 | cellular phone |
| 39 | pager |
| 40 | satellite phone |
| 41 | internet-connected device |
| 42 | memory source |

-continued

ELEMENT LIST

| Element Symbol | Element Name |
| --- | --- |
| 43 | RF module |
| 44 | main board |
| 45 | secondary board |
| 46 | CPU |
| 47 | DSP |
| 48 | user speaker |
| 49 | user microphone |
| 50 | GPS antenna |
| 51 | navigation satellites |
| 52 | power supply |
| 53 | housing |
| 54 | user input |
| 55 | display |
| 56 | top shell |
| 57 | bottom shell |
| 58 | access door |
| 59 | LEDs |
| 60 | ear bud plug |
| 61 | MCU |
| 62 | cradle microphone |
| 63 | cradle speaker |
| 64 | cradle modem |
| 65 | network card |
| 66 | indicator |
| 67 | device connector |
| 68 | secondary connector |
| 69 | cradle power supply |

What is claimed is:

1. A method of providing an emergency contact party telephone line in response to an emergency comprising the steps of:
   providing a user device (21),
   providing a monitoring database (22) including a plurality of contacts and including a first contact method for contacting each contact,
   establishing communication between the user device (21) and the monitoring database (22),
   establishing an emergency condition with the user device (21),
   sending an emergency notification from the user device (21) to the monitoring database (22),
   automatically establishing a support line with the monitoring database (22),
   automatically sending a notification message to each of the contacts with the first contact method,
   automatically providing each of the contacts that accepted the notification message through the first contact method with a route to connect to the support line,
   and characterized by
   automatically sending a notification message through the second contact method different than the first contact method to each of the contacts that failed to respond to the notification message sent through the first contact method; and
   automatically providing each of the contacts that accepted the notification message through the second contact method with a route to connect to the support line through the second contact method.

2. The method as set forth in claim 1 further including the step of arranging the contact methods for each contact into a hierarchy including the first contact method and the second contact method.

3. The method as set forth in claim 1 wherein the user device (21) includes a user input (54) and wherein the step of establishing the emergency condition is further defined as establishing an emergency condition with the user device (21) in response to the user signaling an emergency condition with the user input (54).

4. The method as set forth in claim 1 further including the step of providing at biometric equipment (26) for sensing an emergency and wherein the step of establishing the emergency condition is further defined as establishing an emergency condition with the user device (21) in response to the biometric equipment (26) sensing an emergency condition.

5. The method as set forth in claim 1 wherein the user device (21) includes a GPS receiver (24) and further including the step of establishing a geofence of longitudinal and latitudinal coordinates for containing the user device (21) and wherein the step of establishing the emergency condition is further defined as establishing an emergency condition with the user device (21) in response to the user device (21) leaving the geofence.

6. The method as set forth in claim 1 wherein the route to connect to the support line is a call-in number and a password.

7. The method as set forth in claim 1 further including the step of establishing an Internet (23) Protocol (IP) address for the user device (21) to connect the user device (21) to the Internet (23).

8. The method as set forth in claim 7 further including the step of establishing an Internet (23) Protocol (IP) address for the monitoring database (22) to connect the monitoring database (22) to the Internet (23).

9. The method as set forth in claim 7 wherein the step of establishing an Internet (23) Protocol (IP) address for the user device (21) is further defined as establishing an Internet (23) Protocol (IP) address for the user device (21) through at least one of a cellular network connection and a satellite (33) connection and a cradle (34) connection.

10. The method as set forth in claim 1 wherein the plurality of contact methods include at least two of a phone number for calling the contact and a phone number for sending an SMS message to the contact and a pager (39) number for sending a pager (39) message to the contact and an email address for sending an email message to the contact.

11. A method of providing an emergency contact party telephone line in response to an emergency comprising the steps of:
   providing a user device (21) including a power supply (52) and including a user input (54) for signaling an emergency condition and including biometric equipment (26) and including a GPS receiver (24) and including a microphone and including a speaker,
   establishing a geofence of longitudinal and latitudinal coordinates for containing the user device (21),
   establishing an Internet Protocol (IP) address for the user device (21) through at least one of a cellular network connection and a satellite (33) connection and a cradle (34) connection to connect the user device (21) to the Internet (23),
   providing a monitoring database (22),
   storing a plurality of contacts and a plurality of contact methods for contacting each contact and wherein the plurality of contact methods includes at least two of a phone number for calling the contact and a phone number for sending an SMS message to the contact and a pager number for sending a pager message to the contact and an email address for sending an email message to the contact,
   arranging the contact methods for each contact into a hierarchy including a first contact method and a second contact method, establishing an Internet Protocol (IP) address for the monitoring database (22) to connect the monitoring database (22) to the Internet (23),
connecting the monitoring database (22) to the public switch telephone network,
establishing communication over the Internet (23) between the monitoring database (22) and the user device (21),
determining the longitudinal and latitudinal coordinates of the user device (21) with the GPS receiver (24),
comparing the longitudinal and latitudinal coordinates of the user device (21) to the geofence,
sensing a medical condition with the biometric equipment (26),
establishing an emergency condition with the user device (21) in response to at least one of the user of the user device (21) signaling an emergency condition with the user input (54) and one of the sensors sensing an emergency and the GPS receiver (24) sensing the user device (21) leaving the geofence,
sending an emergency notification through the Internet (23) from the user device (21) to the monitoring database (22),
automatically establishing a support line with the monitoring database (22) and associating a call-in number and a password with the support line,
automatically sending a notification message with the monitoring database (22) to each of the contacts with the first contact method,
receiving with the monitoring database (22) one of an accepted response and a rejected response from the contacts,
automatically sending the call-in number and the password of the support line with the first contact method to each of the contacts that accepted the notification message through the first contact method,
and characterized by
automatically sending the notification message with the monitoring database (22) through a second contact method to each of the contacts that failed to respond within a predetermined amount of time,
receiving with the monitoring database (22) one of an accepted response and a rejected response from the contacts,
automatically sending the call-in number and the password of the support line with the second contact method to each of the contacts that accepted the notification message through the second contact method, and
connecting the user device (21) to the support line.

\* \* \* \* \*